(12) United States Patent
Suzuki et al.

(10) Patent No.: US 6,686,134 B2
(45) Date of Patent: Feb. 3, 2004

(54) PHOTOGRAPHIC PROCESSING COMPOSITION CONTAINING HETEROCYCLE COMBINATION AND METHOD OF FORMING IMAGE

(75) Inventors: Makoto Suzuki, Minami-Ashigara (JP); Yasufumi Nakai, Minami-Ashigara (JP); Yoshiharu Yabuki, Minami-Ashigara (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 10/463,336

(22) Filed: Jun. 18, 2003

(65) Prior Publication Data

US 2003/0224300 A1 Dec. 4, 2003

Related U.S. Application Data

(62) Division of application No. 10/108,900, filed on Mar. 29, 2002.

(30) Foreign Application Priority Data

Mar. 30, 2001 (JP) ........................................ 2001-102469

(51) Int. Cl.$^7$ ................................................. G03C 7/30
(52) U.S. Cl. ....................................................... 430/429
(58) Field of Search .......................................... 430/429

(56) References Cited

U.S. PATENT DOCUMENTS

| 5,994,375 A | 11/1999 | Kochanny et al. |
| 6,153,350 A | 11/2000 | Sezi et al. |
| 6,153,364 A | 11/2000 | Goswami et al. |
| 6,153,365 A | 11/2000 | Goswami et al. |
| 6,262,088 B1 | 7/2001 | Phillips |

*Primary Examiner*—Hoa Van Le
(74) *Attorney, Agent, or Firm*—Sughrue Mion, PLLC

(57) ABSTRACT

A photographic processing composition for silver halide color photographic lightsensitive material, comprising at least one compound represented by the formula (I):

$$A_1\text{—}X\text{—}L\text{—}Y\text{—}A_2 \qquad (I)$$

wherein each of $A_1$ and $A_2$ independently represents an aryl group or an aromatic heterocyclic group, L represents an aromatic heterocyclic group, with the proviso that a triazine ring is not represented thereby, and each of X and Y independently represents O, S or $NR_1$, wherein $R_1$ represents a hydrogen atom or an alkyl group having 1 to 6 carbon atoms, with the proviso that the molecule of the formula (I) has a substituent containing at least one of —OH, —$CO_2M$ and —$SO_3M$ groups, wherein M represents a hydrogen atom, an alkali metal, an alkaline earth metal, an ammonium or a pyridinium, and provided that the molecule of the formula (I) has no azo group.

9 Claims, No Drawings

PHOTOGRAPHIC PROCESSING COMPOSITION CONTAINING HETEROCYCLE COMBINATION AND METHOD OF FORMING IMAGE

CROSS-REFERENCE TO RELATED APPLICATIONS

This is a divisional of application Ser. No. 10/108,900 filed Mar. 29, 2002; the disclosure of which is incorporated herein by reference.

This application is based upon and claims the benefit of priority from the prior Japanese Patent Application No. 2001-102469, filed Mar. 30, 2001, the entire contents of which are incorporated herein by reference.

BACKGROUND OF THE INVENTION

1. Field of the Invention

The present invention relates to a processing composition for silver halide color photographic lightsensitive material. More particularly, the present invention relates to a processing composition which is excellent in the capability of reducing stain attributed to sensitizing dyes remaining in the lightsensitive material after the processing thereof and which is free of any precipitation deposits during the low-temperature storage thereof.

2. Description of the Related Art

Under the circumstances wherein digital cameras and color printers are making striking progress, in the processing of silver halide color photographic lightsensitive materials, it is desired to speedily supply images of high quality to customers. However, simple time reduction in the conventional processing procedure would cause termination of processing before satisfactory washing away of sensitizing dyes from the lightsensitive material with the result that, on a white ground of color print, images would be colored by a large amount of residual sensitizing dyes to thereby become unbearable for appreciation. Further, with respect to color negative films, there have occurred such occasions that the density of minimum density portions is increased with the result that a color balance is deteriorated to thereby disenable providing appropriate prints.

Moreover, in recent years, the use of tabular silver halide grains, presenting an important fundamental technology for highly sensitive photographic lightsensitive materials, increases the amount of sensitizing dyes remaining in the lightsensitive material after the processing thereof, although it enables increasing the amount of sensitizing dyes used per volume so as to exert the effect of enhancing the photographic speed and the ratio of photographic speed to graininess. An increase of the amount of residual sensitizing dyes cannot be ignored depending on processing conditions, and would result in occurrence of phenomena such as a density increase at minimum density portions of color negative films and coloring of highlight portions of color reversal films.

Research Disclosure 20733 discloses the method of using a bistriazinylaminostilbenedisulfonic acid compound as an example of means for removing any residual color attributed to sensitizing dyes. This method has widely been employed in the processing of color photographic lightsensitive materials. Jpn. Pat. Appln. KOKAI Publication No. (hereinafter referred to as JP-A-) 6-329936 discloses a bistriazinylaminostilbenedisulfonic acid compound which has high solubility and is capable of reducing the residual color even in the expedited processing. Further, U.S. Pat. Nos. 6,153,364 and 6,153,365 proposed methods of reducing the residual color with the use of highly stable compounds of novel structure.

However, there is a demand for further concentrating of the processing composition from the viewpoint of reduction of waste containers, recycling facilitation, reduction of transport and storage costs, etc. Any compound which is stably dissolved under a condition of high salt concentration after concentrating and exerts satisfactory effects even in the expedited processing when used below solubility, and which is excellent in the compound stability during storage has not yet been found.

BRIEF SUMMARY OF THE INVENTION

Accordingly, it is an object of the present invention to provide a processing composition for silver halide color photographic lightsensitive material, which enables reducing stain attributed to sensitizing dyes remaining in the lightsensitive material after the processing thereof and which is free of any precipitation deposits during the low-temperature storage thereof.

This object has been attained by the following invention.

(1) A photographic processing composition for silver halide color photographic lightsensitive material, comprising at least one compound represented by the formula (I):

$$A_1\text{—}X\text{—}L\text{—}Y\text{—}A_2 \qquad (I)$$

wherein each of $A_1$ and $A_2$ independently represents an aryl group or an aromatic heterocyclic group; L represents an aromatic heterocyclic group, with the proviso that a triazine ring is not represented thereby; and each of X and Y independently represents O, S or $NR_1$, wherein $R_1$ represents a hydrogen atom or an alkyl group having 1 to 6 carbon atoms, with the proviso that the molecule of the formula (I) has a substituent containing at least one of —OH, —$CO_2M$ and —$SO_3M$ groups, wherein M represents a hydrogen atom, an alkali metal, an alkaline earth metal, an ammonium or a pyridinium, and provided that the molecule of the formula (I) has no azo group.

(2) The photographic processing composition according to item (1) above, wherein, in the formula (I), L is a pyridinediyl group, a pyrazinediyl group, a pyrimidinediyl group, a pyridazinediyl group or a phthalazinediyl group.

(3) The photographic processing composition according to item (1) or (2) above, for use in color development processing.

(4) The photographic processing composition according to item (1) or (2) above, for use in bleach processing or bleach-fix processing.

(5) The photographic processing composition according to item (1) or (2) above, for use in fixing processing.

(6) The photographic processing composition according to item (1) above, for use in a use solution in which the concentration of compound represented by the formula (I) is in a range of 0.05 to 20 mmol/L.

(7) A method of forming an image, comprising using the photographic processing composition for silver halide color photographic lightsensitive material according to any of items (1) to (6) above.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

The general formula (1) will be described in detail below.

Each of $A_1$ and $A_2$ independently represents an aryl group or an aromatic heterocyclic group. The aryl group is preferably a substituted aryl group having 6 to 20 carbon atoms, more preferably 6 to 10 carbon atoms, and most preferably 6 to 8 carbon atoms, which is, for example, 3-carboxyphenyl, 4-carboxyphenyl, 3,5-dicarboxyphenyl, 4-methoxyphenyl, 2-sulfophenyl, 4-sulfophenyl or 5,7-disulfo-2-naphthyl. The heterocyclic group is preferably a substituted or unsubstituted 5- or 6-membered heterocyclic group having 2 to 20 carbon atoms, more preferably 2 to 10 carbon atoms, and most preferably 2 to 8 carbon atoms, which is, for example, 2-furyl, 2-pyrimidinyl or 2-benzothiazolyl.

The aromatic heterocyclic group represented by L is preferably a substituted or unsubstituted heterocyclic group having 2 to 20 carbon atoms, more preferably 2 to 10 carbon atoms, and most preferably 2 to 8 carbon atoms, which is, for example, 3,5-(1,2,4-triazole)diyl, 3,5-isothiazolediyl, 2,6-pyridinediyl, 2,6-pyrazinediyl, 2,6-pyrimidinediyl, 3,6-pyridazinediyl or 1,4-phthalazinediyl. Provided that a triazine ring is not represented by L.

Each of X and Y independently represents $NR_1$, O or S. The substituent represented by $R_1$ is a hydrogen atom or an alkyl group having 1 to 6 carbon atoms (for example, methyl, ethyl, i-propyl or n-propyl).

The compound represented by the general formula (I) (hereinafter also referred to as "compound of the present invention") has a carboxyl, sulfo or hydroxyl group. This carboxyl, sulfo or hydroxyl group may be in free form or in the form of a salt. In the form of a salt, the counter ion may be selected from among an alkali metal, an alkaline earth metal, ammonium and pyridinium. Of these, an alkali metal and an alkaline earth metal are preferred. Na and K are especially preferred. The above ammonium can be, for example, any of ammonium, triethylammonium and tetrabutylammonium. Of these, ammonium is preferred.

The compound represented by the above general formula (I) has no azo group within its molecule.

Specific examples of the compounds of the present invention will be given below, to which, however, the present invention is in no way limited.

1)

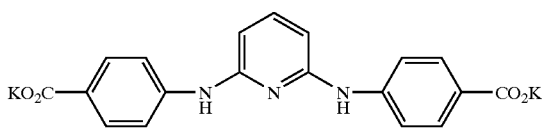

2)

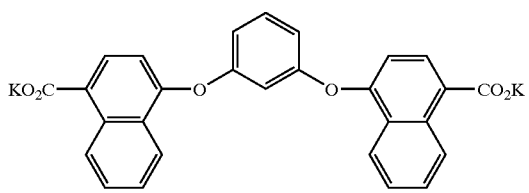

3)

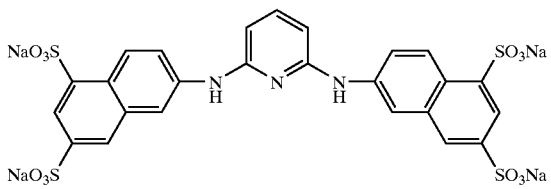

4)

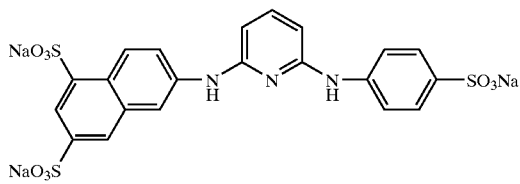

5)

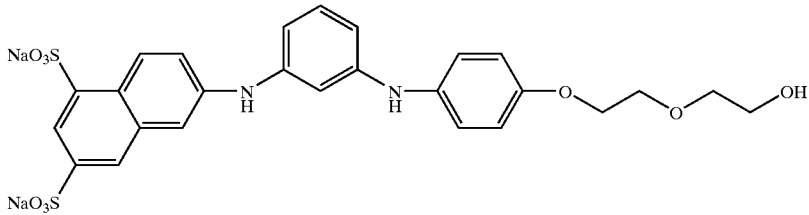

6)

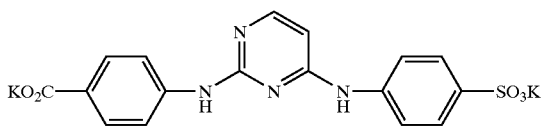

7)

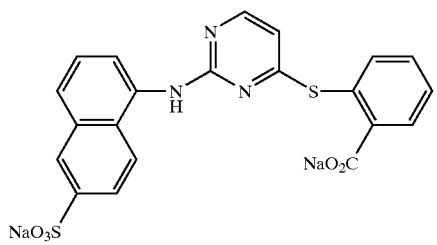

8)
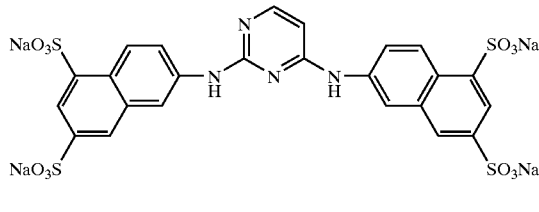
9)
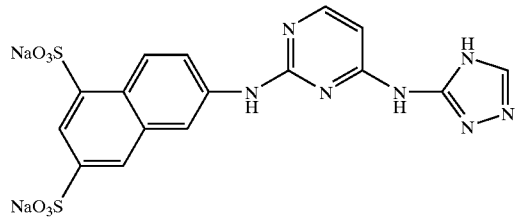
10)
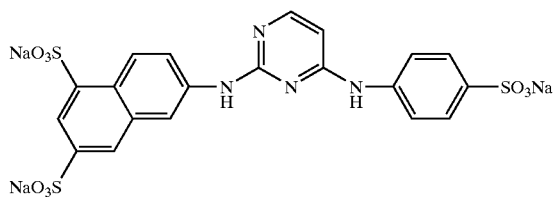
11)
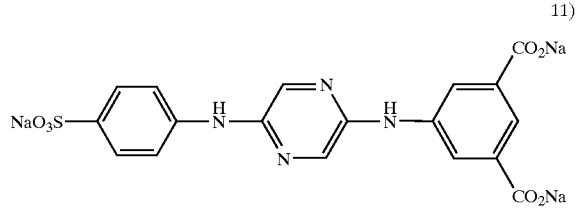
12)
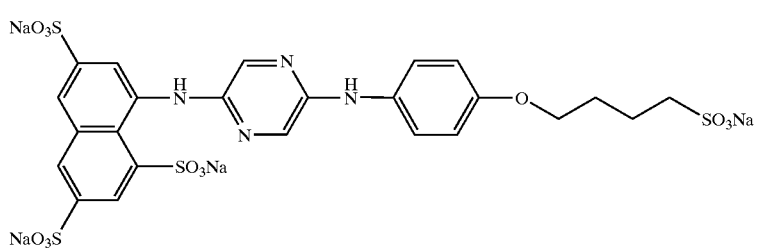
13)
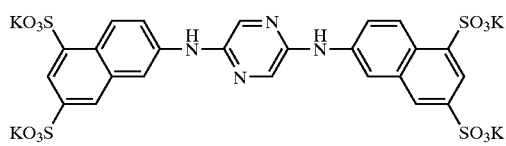
14)
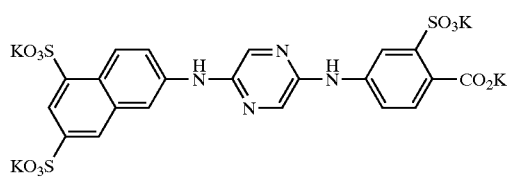
15)
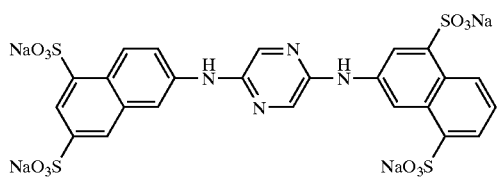
16)
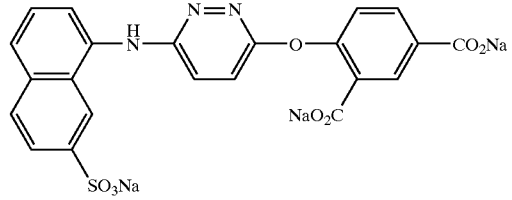
17)
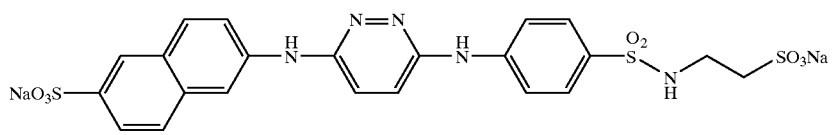
18)
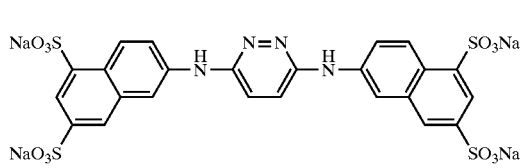
19)
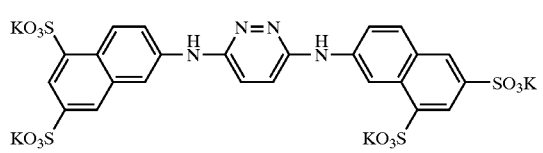

-continued

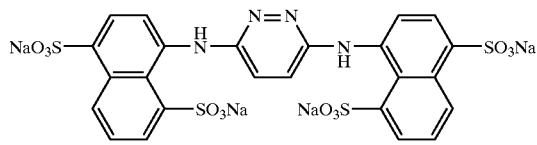
20)

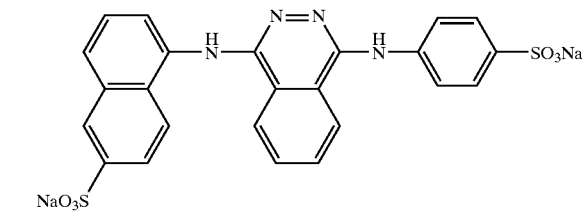
21)

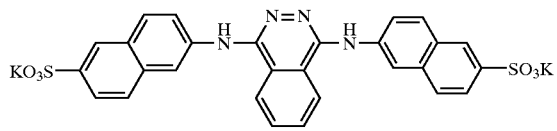
22)

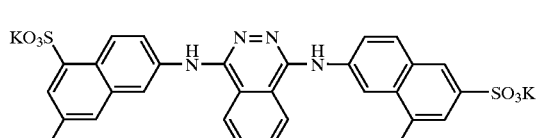
24)

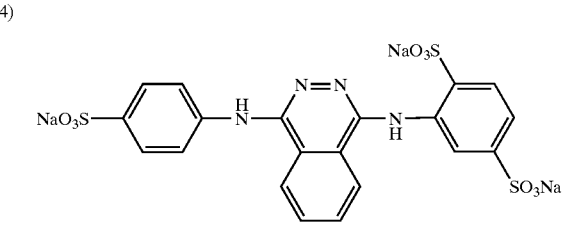
23)

25)

When compounds represented by the general formula (I) of the present invention have a plurality of asymmetric carbon atoms within each molecule thereof, a plurality of stereoisomers exist with respect to each specific structure. The present invention comprehends all the possible stereoisomers. Among a plurality of stereoisomers, only one can be selected and used, or some can be selected and used in the form of a mixture.

Among the compounds represented by the general formula (I) of the present invention, only one can be selected and used, or a plurality thereof can be selected and used in combination. The number of compounds used and the type of processing composition contained can be arbitrarily selected.

The processing composition of the present invention will be described in detail below. The processing composition of the present invention refers to a processing composition characterized by comprising at least one compound represented by the above general formula (I), which processing composition is needed in the processing of silver halide color photographic lightsensitive material for image formation. Specifically, the processing composition of the present invention can be a color development composition, a bleach composition, a bleach-fix composition, a fixing composition, a washing composition or a stabilization composition. Further, the processing composition of the present invention may be a black and white development composition, a reversal composition or a prebleach composition. These processing compositions comprehend preparation compositions. The processing composition of the present invention is preferably a color development composition or a black and white development composition, more preferably a color development composition. In particular, in the application to a color development composition for color print material, the effects of the present invention are especially striking. These processing compositions may be provided at concentrations of solutions fed as a tank solution or replenisher, or may be provided in the form of a concentrate. When the processing composition of the present invention is in the form of a concentrate, it is mixed with water at a given ratio before use as a replenisher or tank solution. The compound of the present invention is characterized in that it is excellent in the precipitation stability in solution-form composition. Therefore, the effects of the present invention are striking in a single liquid or preparation composition in concentrate form. However, the compound of the present invention may be used in various processing compositions having the form of granules, tablets, powder or slurry.

Moreover, the photographic processing composition of the present invention may be an additive composition. The additive composition refers to a composition which is added, before or during the processing, to a tank solution or replenisher needed for the processing of silver halide color photographic lightsensitive material for image formation to thereby function for controlling of photographic performance.

With respect to the processing composition of the present invention, the concentration of compound of the general formula (I) in a use solution is preferably in the range of 0.05 to 20 mmol/L, more preferably 0.15 to 15 mmol/L, and most preferably 0.2 to 10 mmol/L. When the processing composition of the present invention is diluted with water or another processing composition before use, the concentration in the processing composition refers to a value as obtained by multiplying the concentration in use solution by a concentrating ratio.

In the method of forming an image according to the present invention, the processing composition of the present invention is used in at least one processing step. The processing composition of the present invention may be used in a plurality of processing steps or all the processing steps.

With respect to the process for producing the processing composition of the present invention, although quite some methods are available, desirable results can be obtained by the following three methods. However, the process for carrying out the present invention is in no way limited to the following three methods.

(Method A) In this method, a small amount of water is introduced in a mixing vessel in advance, and constituent chemicals are sequentially placed therein under agitation.

(Method B) In this method, constituent chemicals are mixed in a mixing vessel in advance, and thereafter a small amount of water is poured once into the mixture.

(Method C) In this method, constituent chemicals are first divided into appropriate groups, these groups are each dissolved in water or a hydrophilic organic solvent to thereby obtain solutions of high concentration, and the solutions of high concentration are mixed together.

Moreover, processes wherein the above methods are partially utilized can be implemented.

Each of the development composition, bleach composition, bleach-fix composition, fixing composition, washing composition, stabilization composition and additive composition as varied forms of the processing compositions of the present invention will be described below.

The color development composition of the present invention contains a color developing agent. Known aromatic primary amine color developing agents are preferred. p-Phenylenediamine derivatives are especially preferred. Representative examples thereof will be listed below, to which, however, the present invention is in no way limited. In recent years, black and white lightsensitive materials loaded with a coupler which is colored black and developed with common color developer so as to form black and white images are available. The processing composition of the present invention is applicable to these types of lightsensitive materials as well.

Representative examples of the p-phenylenediamine derivatives include:

1) N,N-diethyl-p-phenylenediamine,
2) 4-amino-N,N-diethyl-3-methylaniline,
3) 4-amino-N-(β-hydroxyethyl)-N-methylaniline,
4) 4-amino-N-ethyl-N-(β-hydroxyethyl)aniline,
5) 4-amino-3-methyl-N-ethyl-N-(β-hydroxyethyl)aniline,
6) 4-amino-3-methyl-N-ethyl-N-(3-hydroxypropyl)aniline,
7) 4-amino-3-methyl-N-ethyl-N-(4-hydroxybutyl)aniline,
8) 4-amino-N-ethyl-N-(β-methanesulfonamidoethyl)-3-methylaniline,
9) 4-amino-N,N-diethyl-3-(β-hydroxyethyl)aniline,
10) 4-amino-3-methyl-N-ethyl-N-(β-methoxyethyl)aniline,
11) 4-amino-3-methyl-N-(β-ethoxyethyl)-N-ethylaniline,
12) 4-amino-3-methyl-N-(3-carbamoylpropyl)-N-n-propylaniline,
13) 4-amino-3-methyl-N-(4-carbamoylbutyl)-N-n-propylaniline,
14) N-(4-amino-3-methylphenyl)-3-hydroxypyrrolidine,
15) N-(4-amino-3-methylphenyl)-3-hydroxymethylpyrrolidine, and
16) N-(4-amino-3-methylphenyl)-3-pyrrolidinecarboxamide.

Among these p-phenylenediamine derivatives, compound examples 5), 6), 7), 8) and 12) are preferred. Compound examples 5) and 8) are especially preferred. These p-phenylenediamine derivatives, in the solid state, are generally in the form of, for example, a sulfate, a hydrochloride, a p-toluenesulfonate, a naphthalenedisulfonate or an N,N-bis(sulfonatoethyl)hydroxylamine salt. These p-phenylenediamine derivatives may also be added in free form without having any counter ion. The concentration of aromatic primary amine developing agent mentioned above in each use solution is preferably in the range of 4 to 100 mmol/L, more preferably 6 to 50 mmol/L, and most preferably 8 to 25 mmol/L.

A compound capable of preventing the precipitation of color developing agent may be added to the color development composition of the present invention. As such a compound, there can be mentioned polyethylene glycols, arylsulfonic acids, alkylsulfonic acids, or urea compounds described in JP-A-11-174643. Among these, from the viewpoint of exerting excellent effects with the slightest influence on photographic performance, diethylene glycol, polyethylene glycol 300, p-toluenesulfonic acid and its salts, sulfonic acid substituted with a linear alkyl having 5 to 9 carbon atoms and salts thereof, and ethyleneurea are especially preferred.

The color development composition of the present invention preferably contains a compound capable of preventing the deterioration of color developing agent by air oxidation, namely, a preservative. Sulfites and hydroxylamine are preferably used as an inorganic preservative. These exert conspicuous preserving actions and are preferably used in combination with organic preservatives. Sulfites and hydroxylamine may adversely affect photographic characteristics in the color development step, depending on the lightsensitive material processed. Therefore, there are occasions wherein only either of a sulfite and hydroxylamine is contained, or wherein both are substantially not contained and only an organic preservative is employed.

As the organic preservative, there can preferably be employed hydroxylamine derivatives, hydroxamic acids, hydrazides, phenols, monoamines, diamines, polyamines, alcohols, condensed-ring amines, cyclic amides, salicylic acids, polyethyleneimines, alkanolamines, aromatic polyhydroxy compounds, hydroxylamine derivatives described in JP-A's 3-56456 and 3-33845, and compounds described in JP-A's 3-33846 and 6-148841.

Use of hydroxylamine derivatives in combination with alkanolamines is preferred from the viewpoint that the stability of color developer in a continuous processing is enhanced. Triisopanolamine or triethanolamine can be mentioned as a compound especially preferred for use in combination with hydroxylamines. Also, use in combination with cyclic amide compounds is preferred. Among such compounds, ε-caprolactam is especially preferred.

The pH value of the color development composition of the present invention is preferably in the range of 9.5 to 13.5. The pH value of the color developer prepared therefrom is preferably in the range of 9.0 to 12.2, more preferably 9.9 to 11.2. For maintaining an appropriate pH value, it is preferred to add a buffer. As such a buffer, there can preferably be employed inorganic salts such as sodium and potassium carbonates, bicarbonates, phosphates, borates and tetraborates. Also, organic compounds such as 5-sulfosalicylic acid, β-alanine, proline and trishydroxyaminomethane are preferably used. The buffer for use in the present invention is not limited to these compounds. These buffers are contained in a concentration of 0.1 mol/L or more, preferably in the range of 0.1 to 0.4 mol/L, in terms of concentration of color development replenisher.

Various chelating agents as a suspending agent for potassium, magnesium, etc. can be added to the color development composition of the present invention. A single or a plurality of chelating agents can be used. Examples of preferred chelating agent compounds include nitrilotriacetic acid, diethylenetriaminepentaacetic acid, ethylenediaminetetraacetic acid, N,N,N-trimethylenephosphonic acid, ethylenediamine-N,N,N',N'-tetramethylenesulfonic acid, ethylenediaminesuccinic acid (s, s form), 2-phosphonobutane-1,2,4-tricarboxylic acid, 1-hydroxyethylidene-1,1-diphosphonic acid and 1,2-dihydroxybenzene-4,6-disulfonic acid. The addition amount of chelating agents is satisfactory as long as it is sufficient to cover the metal ions of the color developer. The chelating agents are generally added in an amount of about 0.1 to 10 g/L.

If necessary, an arbitrary development accelerator can be added to the color development composition of the present invention. As the development accelerator, there can be mentioned, for example, polyalkylene oxides, 1-phenyl-3-pyrazolidones, alcohols and carboxylic acids.

If necessary, an arbitrary antifoggant can be added to the color development composition of the present invention. As the antifoggant, there can be mentioned not only metal halides such as sodium chloride, potassium bromide and potassium iodide but also organic antifoggants whose representative compounds are nitrogenous heterocyclic compounds. Examples of the organic antifoggants include benzotriazole, 6-nitrobenzimidazole, 5-nitroisoindazole, 5-methylbenzotriazole, 5-nitrobenzotriazole, 5-chlorobenzotriazole, 2-thiazolylbenzimidazole, 2-thiazolylmethylbenzimidazole, indazole, hydroxyazaindolizine and adenine. Further, other alkylcarboxylic acids, arylcarboxylic acids and saccharides may be added according to necessity.

In the color development to which the present invention applies, with respect to color print lightsensitive materials, the processing temperature is preferably in the range of 30 to 55° C., more preferably 35 to 50° C., and most preferably 38 to 45° C. The development time is preferably in the range of 5 to 90 sec, more preferably 8 to 60 sec, and most preferably 10 to 45 sec. Although the smaller the quantity of replenisher, the greater the preference, it is generally suitable to use 15 to 200 mL of replenisher per m² of lightsensitive material. The quantity of replenisher is preferably in the range of 20 to 120 mL, more preferably 30 to 60 mL.

With respect to color negative films, the processing temperature is preferably in the range of 30 to 55° C., more preferably 35 to 50° C., and most preferably 38 to 45° C. The development time is in the range of 45 sec to 5 min, preferably 60 sec to 4 min, and more preferably 90 sec to 3 min 15 sec. Although the smaller the quantity of replenisher, the greater the preference, it is generally suitable to use 10 to 200 mL of replenisher per 24 exp. The quantity of replenisher is preferably in the range of 12 to 60 mL, more preferably 15 to 30 mL.

With respect to color reversal films, the processing temperature is preferably in the range of 32 to 45° C., more preferably 35 to 40° C., and most preferably 36.5 to 39.5° C. The development time is preferably in the range of 4 to 8 min, more preferably 5 to 7 min, and most preferably 5 min 30 sec to 6 min 30 sec. Although the smaller the quantity of replenisher, the greater the preference, it is generally suitable to use 1000 to 3000 mL of replenisher per m² of lightsensitive material. The quantity of replenisher is preferably in the range of 1500 to 2800 mL, more preferably 2000 to 2400 mL.

The color development composition obtained by concentrating replenishers as described in JP-A's 11-174643, 11-194461 and 11-194462, the disclosures of which are incorporated herein by reference, presents a preferred form of development composition.

The bleaching agent for use in the bleach composition and bleach-fix composition according to the present invention, although known bleaching agents can be used as the same, is preferably selected from among, for example, organic complex salts of iron (III) (for example, complex salts of aminopolycarboxylic acids or other organic acids such as citric acid, tartaric acid and malic acid), persulfates and hydrogen peroxide. Two or more bleaching agents may be used in combination.

Of these, organic complex salts of iron (III) are especially preferred from the viewpoint of speediness and environmental pollution prevention. As the aminopolycarboxylic acids or salts thereof which are useful for forming organic complex salts of iron (III), there can be enumerated not only biodegradable ethylenediaminesuccinic acid (s, s-form), N-(2-carboxylatoethyl)-L-aspartic acid, β-alaninediacetic acid and methyliminodiacetic acid but also compounds such as ethylenediaminetetraacetic acid, diethylenetriaminepentaacetic acid, 1,3-propylenediaminetetraacetic acid, nitrilotriacetic acid, cyclohexanediaminetetraacetic acid and iminodiacetic acid. These compounds may be in the form of any of sodium, potassium, lithium and ammonium salts. Further, a chelating agent may be used in excess of the amount needed for formation of a ferric complex salt. The concentration of bleaching agent in the bleach solution or bleach-fix solution is in the range of 0.01 to 1.0 mol/L, preferably 0.05 to 0.5 mol/L, and more preferably 0.1 to 0.5 mol/L, based on the solution used.

A buffer is preferably added to the bleach composition or bleach-fix composition. The buffer is selected depending on an intended pH value. As preferred buffers, there can be mentioned organic acids such as succinic acid, maleic acid, glycolic acid, malonic acid, fumaric acid, sulfosuccinic acid and acetic acid; organic bases such as imidazole and dimethylimidazole; and compounds represented by the general formulae (A-a) and (B-b) in JP-A-9-211819. The addition amount of these compounds is preferably in the range of 0.005 to 3.0 mol/L, more preferably 0.05 to 1.5 mol/L, based on the solution used. In the bleach solution, the pH value preferably ranges from 2 to 7, more preferably from 3 to 6. In the bleach-fix solution, the pH value preferably ranges from 3 to 8, more preferably from 4 to 7.

In the bleach-fix of color print lightsensitive materials to which the present invention applies, the processing temperature is preferably in the range of 30 to 55° C., more preferably 35 to 50° C., and most preferably 38 to 45° C. The bleach-fix time is preferably in the range of 5 to 90 sec, more preferably 8 to 60 sec, and most preferably 10 to 45 sec. Although the smaller the quantity of replenisher, the greater the preference, it is generally suitable to use 20 to 200 mL of replenisher per m² of lightsensitive material. The quantity of replenisher is preferably in the range of 25 to 120 mL, more preferably 30 to 50 mL.

In the bleach of color negative films, the processing temperature is preferably in the range of 30 to 55° C., more preferably 35 to 50° C., and most preferably 38 to 45° C. The bleach time is preferably in the range of 12 sec to 2 min, more preferably 15 sec to 1 min 15 sec, and most preferably 18 to 60 sec. Although the smaller the quantity of replenisher, the greater the preference, it is generally suitable to use 2.5 to 50 mL of replenisher per 24 exp. The quantity of replenisher is preferably in the range of 3 to 25 mL, more preferably 4 to 12 mL.

In the bleach of color reversal films, the processing temperature is in the range of 30 to 45° C., preferably 33 to 40° C., and more preferably 37 to 39° C. The bleach time is in the range of 4 to 8 min, preferably 5 to 7 min, and more preferably 5 min 30 sec to 6 min 30 sec. Although the smaller the quantity of replenisher, the greater the preference, it is generally suitable to use 160 to 400 mL of replenisher per m² of lightsensitive material. The quantity of replenisher is preferably in the range of 180 to 300 mL, more preferably 200 to 250 mL.

As the fixing agent for use in the bleach-fix composition or fixing composition of the present invention, there can be mentioned known fixing agents, for example, thiosulfates such as sodium thiosulfate and ammonium thiosulfate, thiocyanates such as sodium thiocyanate and ammonium thiocyanate, ethylenebisglycolic acid, 3,6-dithia-1,8-octanediol, thioether compounds and thioureas described in JP-A-4-317055, and water soluble silver halide dissolving agents such as mesoion compounds described in JP-A's 4-143757 and 4-230749. These can be used individually or in combination. It is preferred to use thiosulfates, especially ammonium thiosulfate, as the fixing agent. The concentration of fixing agent in the fixing solution or bleach-fix solution is preferably in the range of 0.3 to 2 mol/L, more preferably 0.5 to 1.5 mol/L.

As aforementioned, a buffer is preferably added to the fixing composition. Likewise, it is preferred to add a buffer to the bleach-fix composition. As preferred buffers, there can be mentioned heterocyclic organic bases such as imidazole and dimethylimidazole, aminoalkylenesulfonic acids such as taurine, and dibasic acids such as succinic acid, maleic acid and malonic acid. The pH value thereof is preferably in the range of 3 to 8, more preferably 4 to 7.

The bleach-fix composition and fixing composition according to the present invention preferably contain, as a preservative, a compound capable of releasing sulfite ions, namely, a sulfite, a bisulfite, a metabisulfite, etc. These are preferably added in the form of a potassium salt, a sodium salt or an ammonium salt. Also, an arylsulfinic acid such as p-toluenesulfinic acid, m-carboxybenzenesulfinic acid or p-aminobenzenesulfinic acid is preferably contained therein. These compounds are preferably contained in a concentration of 0.02 to 1.0 mol/L based on the solution used. Also, other compounds such as ascorbic acid, a carbonyl bisulfuric acid adduct and a carbonyl compound may be added as the preservative.

The bleach-fix composition and fixing composition according to the present invention may be dosed with a mercapto nitrogenous heterocyclic compound, such as mercaptotriazole, aminomercaptotriazole or N-methylmercaptoimidazole, capable of forming stable silver ions in order to improve image storage, and may be dosed with a bisamidine, bisguanidine or monoamidine compound capable of accelerating the washing away of developing agents as described in JP-A-5-303185. Furthermore, if necessary, the bleach-fix composition and fixing composition according to the present invention may be dosed with a polymer such as polyethylene glycol or polyvinylpyrrolidone, a chelating agent, an antifoaming agent, a mildewproofing agent, etc.

In the bleach-fix of color print lightsensitive materials to which the present invention applies, the processing temperature, bleach-fix time and quantity of replenisher are as aforementioned. In the fixing of color negative films, the processing temperature is preferably in the range of 30 to 55° C., more preferably 35 to 50° C., and most preferably 38 to 45° C. The bleach time is preferably in the range of 20 sec to 2 min, more preferably 30 sec to 1 min 40 sec, and most preferably 35 sec to 1 min 20 sec. Although the smaller the quantity of replenisher, the greater the preference, it is generally suitable to use 4 to 60 mL of replenisher per 24 exp. The quantity of replenisher is preferably in the range of 5 to 40 mL, more preferably 6 to 30 mL.

In the fixing of color reversal films, the processing temperature is preferably in the range of 30 to 45° C., more preferably 33 to 40° C., and most preferably 37 to 39° C. The fixing time is preferably in the range of 2 to 6 min, more preferably 3 to 5 min, and most preferably 3 min 30 sec to 4 min 30 sec. Although the smaller the quantity of replenisher, the greater the preference, it is generally suitable to use 800 to 2000 mL of replenisher per m² of lightsensitive material. The quantity of replenisher is preferably in the range of 900 to 1500 mL, more preferably 1000 to 1250 mL.

The washing composition and stabilization composition according to the present invention may be dosed with formalin, acetaldehyde, pyruvinaldehyde, a formaldehyde bisulfuric acid adduct described in U.S. Pat. No. 4,921,779, or an N-methylol compound described in JP-A-5-34889, the disclosures of which are incorporated herein by reference, in order to prevent stain formation or dye discoloration attributed to residual magenta couplers. Also, an arylsulfinic acid such as p-toluenesulfinic acid, m-carboxybenzenesulfinic acid or p-aminobenzenesulfinic acid is preferably contained therein. Further, if necessary, the washing composition and stabilization composition may be dosed with a surfactant as a dewatering agent, a chelating agent as a hard water softener, a buffer for pH adjustment, an antifoaming agent, a mildewproofing agent, an antibacterial agent, etc. The pH value thereof is preferably in the range of 4 to 10, more preferably 5 to 8. The temperature thereof, although set for various values depending on the intended use, properties, etc. of lightsensitive material, is generally in the range of 20 to 50° C., preferably 25 to 45° C.

Photographic elements to be processed by the use of the processing composition of the present invention can comprise any of common silver halides such as silver chloride, silver bromide, silver bromoiodide, silver chlorobromide, silver chloroiodide and mixtures thereof as a lightsensitive material. In one form, the photographic element is one of high silver chloride content containing at least 50 mol % of chlorides, preferably at least 90 mol % of silver chloride, and is often used in, for example, a color print lightsensitive material.

In another form, at least one emulsion consists principally of silver bromide (at least 50 mol % silver bromide). Most preferably, this photographic element has at least one color recording, and each color recording comprises at least one emulsion principally of silver bromide as used in color negative films and color reversal films. The photographic element to be processed according to the present invention can be a monocolor element or multicolor element. Further, this element can include a magnetic recording layer known in the art to which the present invention pertains.

The details of each individual photographic element are described in, for example, Research Disclosures (hereinafter referred to as "RD"). Reference can be made to RD 17643 pages 23 to 27, RD 18716 pages 647 to 650, RD 307105 pages 866 to 868 and pages 873 to 879, and RD 36544 pages 501 to 541. These relate to useful silver halide emulsions (negative type or positive type) and processes for preparing the same, various sensitizers, dye forming couplers, image dye stabilizers, dyes, ultraviolet absorbents, filters, binders, film hardeners, plasticizers, lubricants, coating aids, surfactants, antistatic agents, matting agents, paper and film supports, various image forming methods for negative or positive image forming color elements, etc.

When the processing composition of the present invention is a preparation composition, a configuration wherein all the components to be contained in a use solution are incorporated in a single composition, namely, a one-pack configuration is advantageous. However, when, with respect to, for example, the color development composition or bleach-fix composition, it is not desirable to bring constituent components into contact with each other for a prolonged period of time, it may be appropriate to produce a processing composition of two-pack or three-pack configuration wherein constituent components are separated into two or more liquid agents, or solid agents, or liquid and solid agents. These configurations of preparations are generally designated 1-part, 2-part, 3-part, . . . configurations under the nomenclature of international standards ISO 5989. The processing composition of the present invention is in no way deteriorated, with respect to the invention's effects and characteristics, by being divided into parts. In particular with respect to the color development composition, however, the 1-part configuration is preferred.

The container for the processing composition of the present invention can be constituted of known materials according to the contents intended. The container may be prepared from a single material, or a composite material, for example, a composite material composed of a material of high gas permeability and a material of high alkali resistance. From the viewpoint of reuse and recycle, it is preferred that the container be constituted of a single material. Examples of the materials used for preparing the container include polyester resins, polyolefin resins, acrylic resins, ABS resins, epoxy resins, polyamide resins (such as nylons), polyurethane resins, polystyrene resins, polycarbonate resins, PVA, polyvinyl chloride, polyvinylidene chloride and polyethylene resins. In particular, containers constituted of a single material selected from among polyester resins (such as polyethylene terephthalate and polyethylene naphthalate) and polyolefin resins (such as polyethylene and polypropylene) are preferred. Polyethylene resins are more preferred, and a high-density polyethylene resin (HDPE) is most preferred as the container material.

The material for preparing the container for use in the present invention can be loaded with carbon black, titanium white, a pigment, calcium carbonate, a plasticizer compatible with the material, etc., unless the loading is detrimental to the processing composition. The material for preparing the container is preferably one of 85% or more polyethylene content containing none of plasticizers, more preferably one of 95% or more polyethylene content containing none of plasticizers.

The shape and structure of containers for accommodating the processing composition of the present invention can be arbitrarily designed in conformity with the object. Use can be made of not only bottles of regular shape but also expandable containers described in JP-A-1-235950, containers with flexible partition walls described in JP-A-62-134626, etc. Containers of JP-A-11-282148 are especially preferred as the container for accommodating the processing composition of the present invention from the viewpoint of capacity, space efficiency, self-supporting capability, shape retention, reuse and recycle. A kit comprising a single cartridge and, assembled therein, containers of the same shape and volume constituted of a single material wherein a plurality of compositions according to the present invention are accommodated presents a preferred form. The cartridge of JP-A-2000-3014 can be mentioned as an example thereof. In the cartridge, the combination of processing compositions can be arbitrarily selected. The cartridges of JP-A'S 11-295858 and 11-288068 present preferred forms wherein the development composition, bleach composition and fixing composition are incorporated.

The present invention will be described in greater detail below while indicating the stability against deposit precipitation and photographic properties of processing compositions with respect to the following Examples, to which, however, the present invention is in no way limited.

EXAMPLE 1

(1) Preparation of Color Development Composition

| Compound of the invention see Table 1 | |
|---|---|
| Brightening agent | (FL-1) 1.75 g |
| Triisopropanolamine | 34.0 g |
| Ethylenediaminetetraacetic acid | 15.0 g |
| Sodium sulfite | 0.80 g |
| Polyethylene glycol (av. MW: 300) | 40.0 g |
| Sodium 4,5-dihydroxybenzene-1,3-disulfonate | 2.0 g |
| Disodium-N,N-bis(sulfonatoethyl)hydroxylamine | 55.0 g |
| 4-Amino-3-methyl-N-ethyl-N-(β-methanesulfonamidoethyl)aniline.3/2sulfate.monohydrate | 55.0 g |
| Potassium hydroxide | 19.0 g |
| Sodium hydroxide | 24.0 g |
| Potassium carbonate | 100.0 g |
| Water | q.s. ad 1000 mL |
| pH | 13.2. |

-continued

Compound of the invention see Table 1

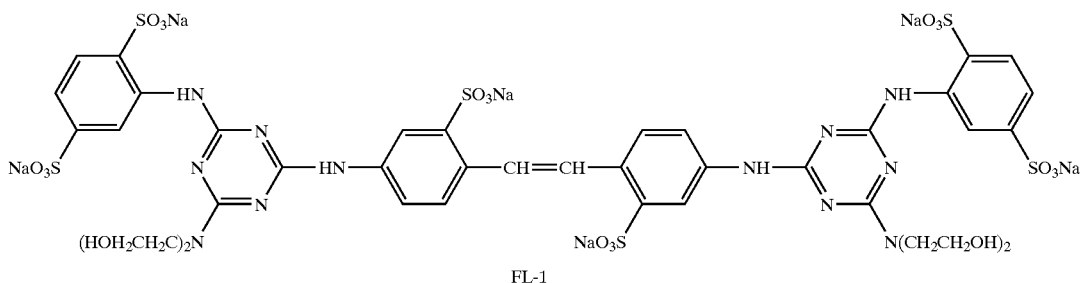

FL-1

(2) Preparation of Lightsensitive Material Sample

One side of a support comprising a paper having its both major surfaces covered with a polyethylene resin was treated by corona discharge, furnished with a gelatin substratum layer containing sodium dodecylbenzenesulfonate, and further sequentially coated to provide the 1st to 7th layers. Thus, silver halide color photographic lightsensitive material P-1 of the following layer arrangement was obtained. The coating liquid for each photographic constituting element layer was prepared in the following manner.

Preparation of 5th Layer Coating Liquid 300 g of cyan coupler (ExC), 250 g of dye image stabilizer (Cpd-1), 30 g of dye image stabilizer (Cpd-14), 100 g of dye image stabilizer (Cpd-15), 80 g of dye image stabilizer (Cpd-16), 50 g of dye image stabilizer (Cpd-17) and 10 g of dye image stabilizer (Cpd-18) were dissolved in 230 g of solvent (Solv-6) and 350 mL of ethyl acetate, and emulsified in 6500 g of a 10% aqueous gelatin solution containing 25 g of sodium dodecylbenzenesulfonate. Thus, emulsified dispersion C was obtained.

Separately, there was prepared silver chlorobromide emulsion C (cubic form; 5:5 (silver molar ratio) mixture of large-size emulsion C of 0.40 μm average grain size and small-size emulsion C of 0.30 μm average grain size, the variation coefficients of grain size distribution thereof being 0.09 and 0.11, respectively; and with respect to both the large-size and small-size emulsions, 0.5 mol % of silver bromide localized on part of the surface of grains based on silver chloride emulsion).

In this emulsion, each of the following red-sensitive sensitizing dyes G and H was added to the large-size emulsion C in an amount of, per mol of silver, $9.0 \times 10^{-5}$ mol, and added to the small-size emulsion C in an amount of $12.0 \times 10^{-5}$ mol. The optimum chemical ripening of this emulsion was performed by adding a sulfur sensitizer and a gold sensitizer.

Mixing and dissolution of the above emulsified dispersion C and silver chlorobromide emulsion C were effected to thereby obtain the 5th layer coating liquid of the following composition. The coating amount of emulsion is in terms of silver quantity.

The coating liquids for the 1st to 4th layers, the 6th layer and the 7th layer were prepared in the same manner as the coating liquid for the 5th layer. 1-oxy-3,5-dichloro-s-triazine sodium salt was used as a gelatin hardener of each of the layers, and, to each of the layers, Ab-1, Ab-2, Ab-3 and Ab-4 were added in a total amount of 15.0 mg/m², 60.0 mg/m², 5.0 mg/m² and 10.0 mg/m², respectively.

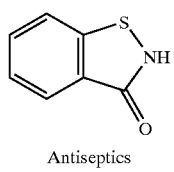

Antiseptics (Ab-1)

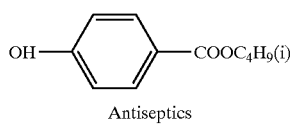

Antiseptics (Ab-2)

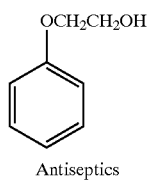

Antiseptics (Ab-3)

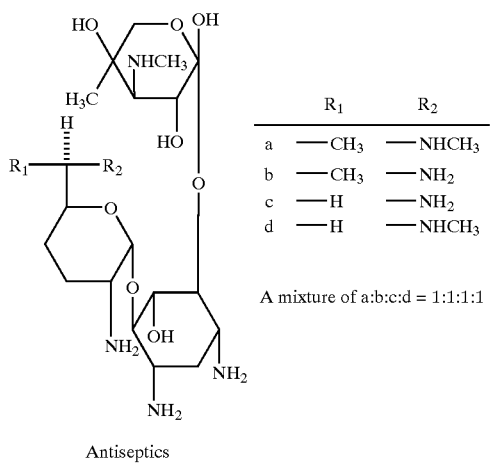

Antiseptics (Ab-4)

| | $R_1$ | $R_2$ |
|---|---|---|
| a | —CH₃ | —NHCH₃ |
| b | —CH₃ | —NH₂ |
| c | —H | —NH₂ |
| d | —H | —NHCH₃ |

A mixture of a:b:c:d = 1:1:1:1

The silver chlorobromide emulsion of each lightsensitive emulsion layer was loaded with the following spectral sensitizing dyes.

Blue-sensitive Emulsion Layer

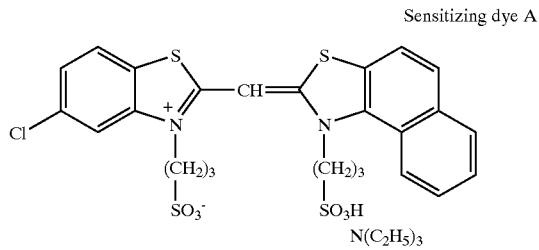

Sensitizing dye A

Sensitizing dye B

Sensitizing dye C (Each of the sensitizing dyes A and C was added in an amount of, per mol of silver halides, $0.42\times10^{-4}$ mol to the large-size emulsion and $0.50\times10^{-4}$ mol to the small-size emulsion. The sensitizing dye B was added in an amount of, per mol of silver halides, $3.4\times10^{-4}$ mol to the large-size emulsion and $4.1\times10^{-4}$ mol to the small-size emulsion.)

Green-sensitive Emulsion Layer (The sensitizing dye D was added in an amount of, per mol of silver halides, $3.0\times10^{-4}$ mol to the large-size emulsion and $3.6\times10^{-4}$ mol to the small-size emulsion. The sensitizing dye E was added in an amount of, per mol of silver halides, $4.0\times10^{-4}$ mol to the large-size emulsion and $7.0\times10^{-5}$ mol to the small-size emulsion. The sensitizing dye F was added in an amount of, per mol of silver halides, $2.0\times10^{-4}$ mol to the large-size emulsion and $2.8\times10^{-4}$ mol to the small-size emulsion.)

Red-sensitive Emulsion Layer

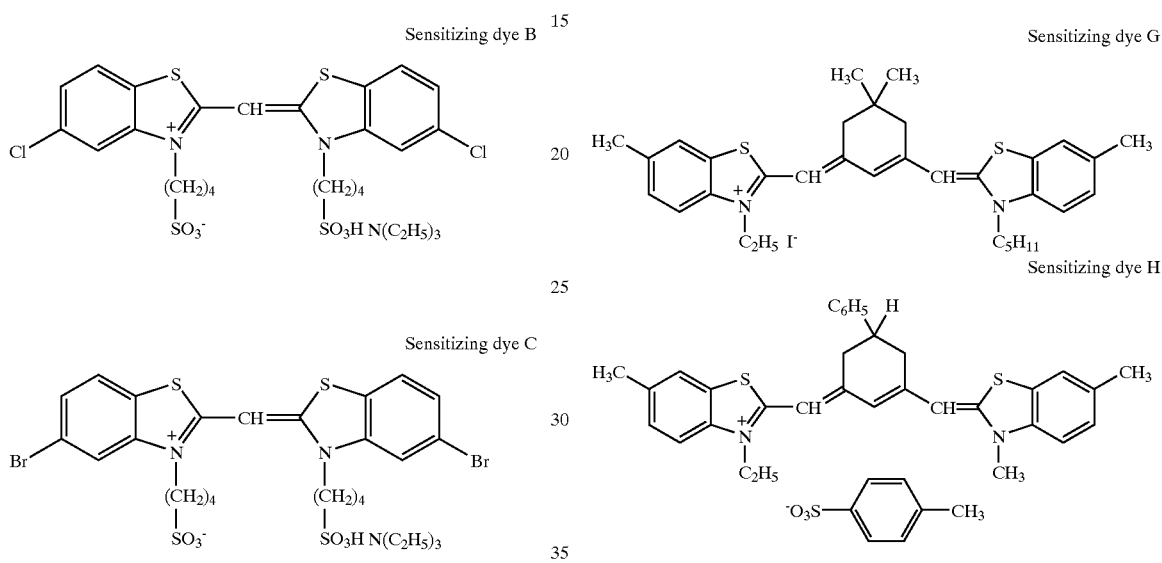

Sensitizing dye G

Sensitizing dye H (Each of the sensitizing dyes G and H was added in an amount of, per mol of silver halides, $8.0\times10^{-5}$ mol to the large-size emulsion and $10.7\times10^{-4}$ mol to the small-size emulsion. Further, the following compound I was added to the red-sensitive emulsion layer in an amount of 3.0 (ml $10^{-3}$ mol per mol of silver halides.)

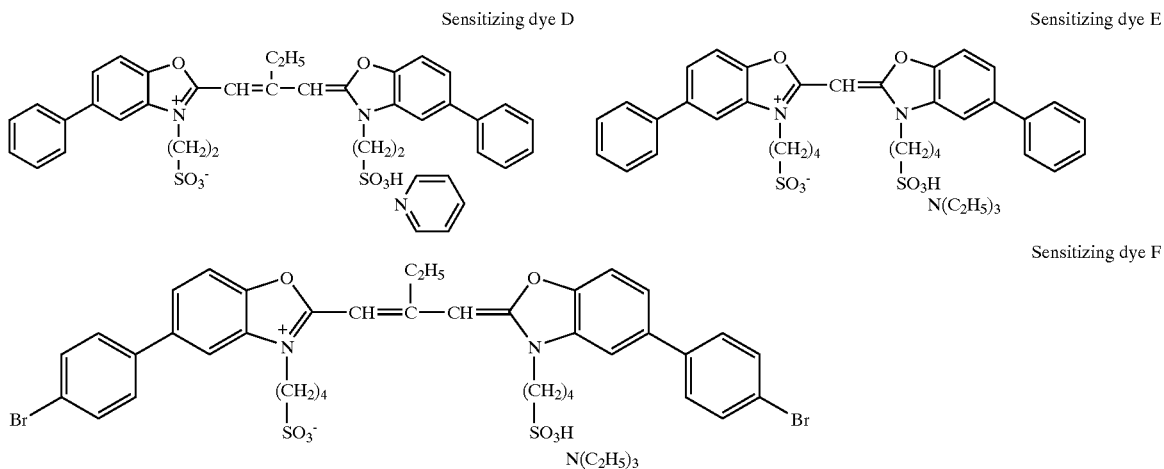

Sensitizing dye D

Sensitizing dye E

Sensitizing dye F

Compound I

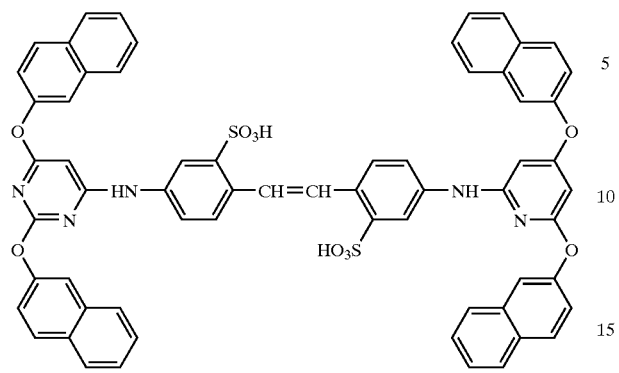

The blue-sensitive emulsion layer (1st layer), green-sensitive emulsion layer (3rd layer) and red-sensitive emulsion layer (5th layer) were loaded with 1-(3-methylureidophenyl)-5-mercaptotetrazole in an amount of $3.3 \times 10^{-4}$ mol, $1.0 \times 10^{-3}$ mol and $5.9 \times 10^{-4}$ mol, respectively, per mol of silver halides.

The 2nd layer, 4th layer, 6th layer and 7th layer were loaded with the above compound in an amount of 0.2 mg/m$^2$, 0.2 mg/m$^2$, 0.6 mg/m$^2$ and 0.1 mg/m$^2$, respectively.

The blue-sensitive emulsion layer and green-sensitive emulsion layer were loaded with 4-hydroxy-6-methyl-1,3,3a,7-tetrazaindene in an amount of $1 \times 10^{-4}$ mol and $2 \times 10^{-4}$ mol, respectively, per mol of silver halides.

The red-sensitive emulsion layer was loaded with a latex of methacrylic acid/butyl acrylate copolymer (weight ratio 1:1, average molecular weight 200,000 to 400,000) in an amount of 0.05 g/m$^2$.

The 2nd layer, 4th layer and 6th layer were loaded with disodium catechol-3,5-disulfonate in an amount of 6 mg/m$^2$, 6 mg/m$^2$ and 18 mg/m$^2$, respectively.

For irradiation prevention, the following dyes (the coating amount indicated in parentheses) were added.

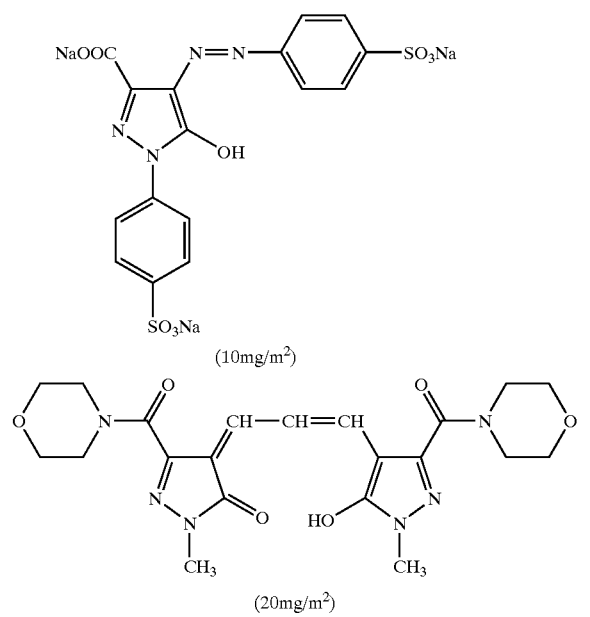

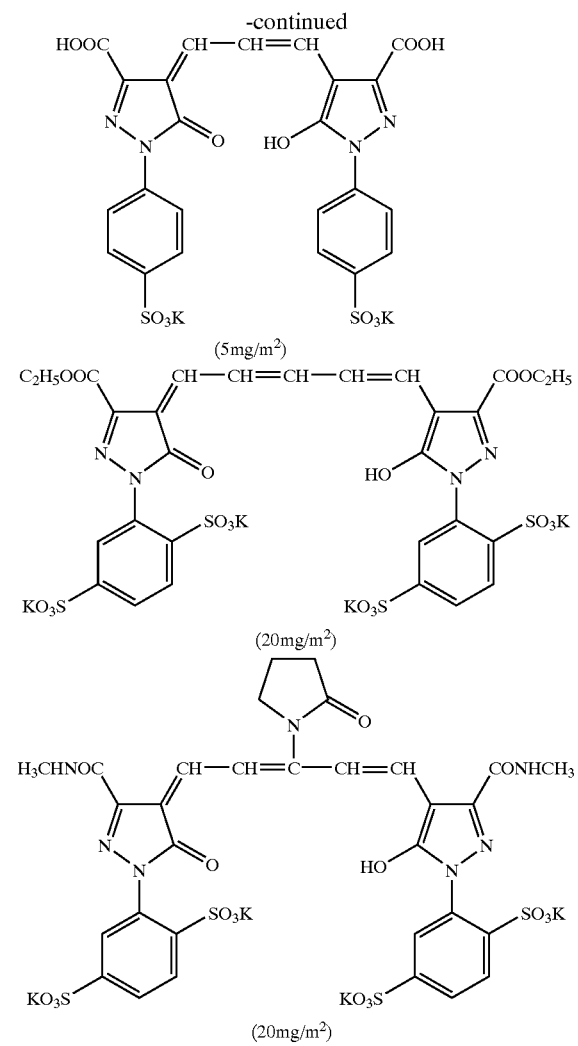

(Layer Arrangement)

The constitution of each layer is specified below. The numerals indicate the coating amount (g/m$^2$) With respect to the silver halide emulsions, the coating amount is in terms of silver.

Support

Polyethylene Resin Laminated Paper (polyethylene resin on the 1st layer side contains white pigment (TiO$_2$:16% by weight content and ZnO: 4% by weight content), brightening agent (4,4'-bis(5-methylbenzoxazolyl)stilbene: 0.03% by weight content) and bluish dye (ultramarine)).

---

1st layer (blue-sensitive emulsion layer)

Silver chlorobromide emulsion A (cubic form; 5:5     0.24
(silver molar ratio) mixture of large-size emulsion A
of 0.74 μm average grain size and small-size emulsion A
of 0.65 μm average grain size, the variation
coefficients of grain size distribution thereof being
0.08 and 0.10, respectively; and with respect to both -continued

| | |
|---|---|
| the large-size and small-size emulsions, 0.3 mol % of silver bromide localized on part of the surface of grains based on silver chloride) | |
| Gelatin | 1.25 |
| Yellow coupler (ExY) | 0.57 |
| Dye image stabilizer (Cpd-1) | 0.07 |
| Dye image stabilizer (Cpd-2) | 0.04 |
| Dye image stabilizer (Cpd-3) | 0.07 |
| Solvent (Solv-1) | 0.21 |
| 2nd layer (color mixing inhibiting layer) | |
| Gelatin | 0.99 |
| Color mixing inhibitor (Cpd-4) | 0.09 |
| Color mixing inhibitor (Cpd-5) | 0.018 |
| Stabilizer (Cpd-6) | 0.13 |
| Color mixing inhibitor (Cpd-7) | 0.01 |
| Solvent (Sov-1) | 0.06 |
| Solvent (Sov-2) | 0.22 |
| 3rd layer (green-sensitive emulsion layer) | |
| Silver chlorobromide emulsion B (cubic form; 1:3 (silver molar ratio) mixture of large-size emulsion B of 0.45 μm average grain size and small-size emulsion B of 0.35 μm average grain size, the variation coefficients of grain size distribution thereof being 0.10 and 0.08, respectively; and with respect to both the large-size and small-size emulsions, 0.4 mol % of silver bromide localized on part of the surface of grains based on silver chloride) | 0.14 |
| Gelatin | 1.36 |
| Magenta coupler (ExM) | 0.15 |
| Ultraviolet absorbent (UV-1) | 0.05 |
| Ultraviolet absorbent (UV-2) | 0.03 |
| Ultraviolet absorbent (UV-3) | 0.02 |
| Ultraviolet absorbent (UV-4) | 0.04 |
| Dye image stabilizer (Cpd-2) | 0.02 |
| Color mixing inhibitor (Cpd-4) | 0.002 |
| Stabilizer (Cpd-6) | 0.09 |
| Dye image stabilizer (Cpd-8) | 0.02 |
| Dye image stabilizer (Cpd-9) | 0.03 |
| Dye image stabilizer (Cpd-10) | 0.01 |
| Dye image stabilizer (Cpd-11) | 0.0001 |
| Solvent (Solv-3) | 0.11 |
| Solvent (Solv-4) | 0.22 |
| Solvent (Solv-5) | 0.20 |
| 4th layer (color mixing inhibiting layer) | |
| Gelatin | 0.71 |
| Color mixing inhibitor (Cpd-4) | 0.06 |
| Color mixing inhibiting aid (Cpd-5) | 0.013 |
| Stabilizer (Cpd-6) | 0.10 |
| Color mixing inhibitor (Cpd-7) | 0.007 |
| Solvent (Solv-1) | 0.04 |
| Solvent (Solv-2) | 0.16 |
| 5th layer (red-sensitive emulsion layer) | |
| Silver chlorobromide emulsion C (cubic form; 5:5 (silver molar ratio) mixture of large-size emulsion C of 0.40 μm average grain size and small-size emulsion C of 0.30 μm average grain size, the variation coefficients of grain size distribution thereof being 0.09 and 0.11, respectively; and with respect to both the large-size and small-size emulsions, 0.5 mol % of silver bromide localized on part of the surface of grains based on silver chloride) | 0.20 |
| Gelatin | 1.11 |
| Cyan coupler (ExC-1) | 0.15 |
| Cyan coupler (ExC-2) | 0.10 |
| Dye image stabilizer (Cpd-1) | 0.25 |
| Dye image stabilizer (Cpd-14) | 0.03 |
| Dye image stabilizer (Cpd-15) | 0.10 |
| Dye image stabilizer (Cpd-16) | 0.08 |
| Dye image stabilizer (Cpd-17) | 0.05 |
| Dye image stabilizer (Cpd-18) | 0.01 |
| Solvent (Solv-5) | 0.23 |

-continued

| | |
|---|---|
| 6th layer (ultraviolet absorbing layer) | |
| Gelatin | 0.46 |
| Ultraviolet absorbent (UV-1) | 0.14 |
| Ultraviolet absorbent (UV-2) | 0.05 |
| Ultraviolet absorbent (UV-3) | 0.04 |
| Ultraviolet absorbent (UV-4) | 0.06 |
| Solvent (Solv-7) | 0.25 |
| 7th layer (protective layer) | |
| Gelatin | 1.00 |
| Acrylic denatured copolymer of poly (vinyl alcohol) (degree of denaturation 17%) | 0.04 |
| Liquid paraffin | 0.02 |
| Surfactant (Cpd-13) | 0.01 |

(ExY) Yellow Coupler
A mixture of Y1 and Y2 having a molar ratio of 60:40

Y1

$(H_3C)_3C-\overset{O}{\overset{\|}{C}}-CH-\overset{O}{\overset{\|}{C}}-NH-$ [4-Cl-phenyl]-$(t)C_5H_{11}$, $NHCOCHO-$ phenyl-$C_5H_{11}(t)$, $C_2H_5$, $CH_2$-phenyl, $C_2H_5$

Y2

$(H_3C)_3C-\overset{O}{\overset{\|}{C}}-CH-\overset{O}{\overset{\|}{C}}-NH-$ [4-$CH_3O$-phenyl]-$(t)C_5H_{11}$, $NHCOCHO-$ phenyl-$C_5H_{11}(t)$, $C_2H_5$ (ExM) Magenta Coupler
A mixture of M1 and M2 having a molar ratio of 60:40

M1

$(t)C_4H_9$, Cl, pyrazolotriazole-NH, phenyl-$NHCOCH_2CH_2COOC_{14}H_{29}$

M2

$H_3C$, Cl, pyrazolotriazole-NH, $CHCH_2NHCOCHO-$ phenyl-$C_5H_{11}(t)$, $(t)C_5H_{11}$, $CH_3$, $C_6H_{13}$ (ExC) Cyan Coupler A mixture of ExC-1 and ExC-2 having a molar ratio of 60:40

ExC-1

ExC-2

A mixture of having a molar ratio of 1:1:1

(Cpd-1) Number average molecular weight: 50,000
Dye image stabilizer (Cpd-2)
Dye image stabilizer (Cpd-3) n = 7~8 (average)
Dye image stabilizer (Cpd-5)
Color mixing inhibitor (Cpd-6) Number average molecular weight: 600 m/n = 10/90
Stabilizer (Cpd-7)
Color mixing inhibitor (Cpd-8)
Dye image stabilizer (Cpd-9)
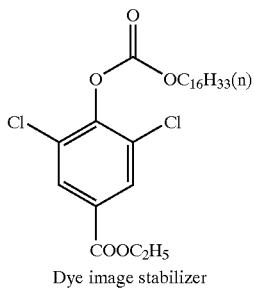
Dye image stabilizer
(Cpd-10)
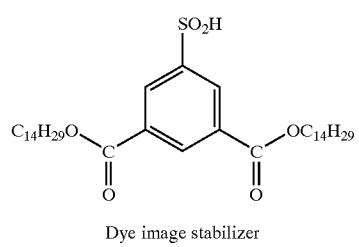
Dye image stabilizer
(Cpd-11)
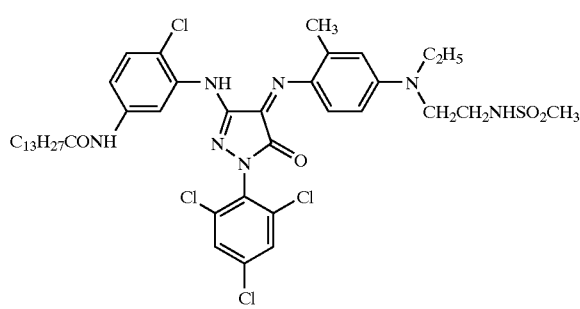
A mixture of
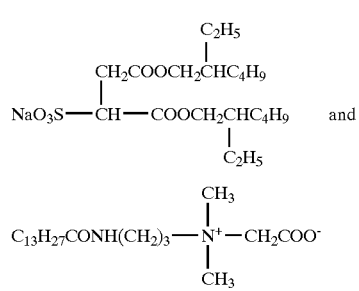
having a molar ratio of 7:3
(Cpd-14)
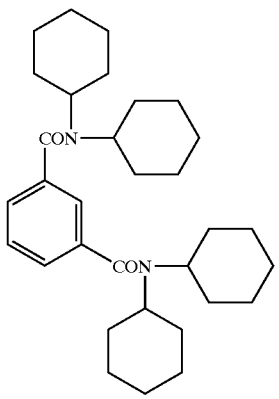
(Cpd-15)
A mixture of 
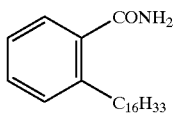
and 
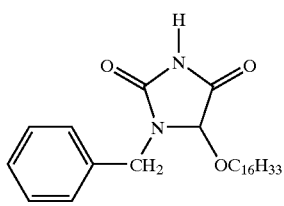
having a molar ratio of 1:1
having a molar ratio of 1:1
(Cpd-16)
(Cpd-17)
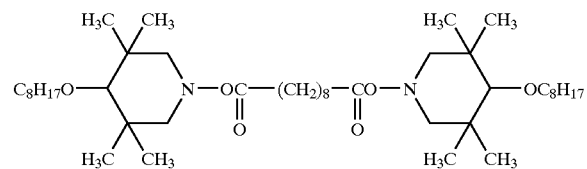
(Cpd)-18
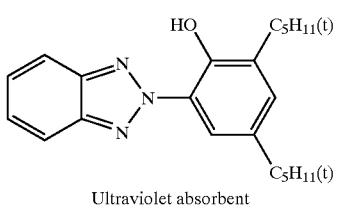
(UV-1)
Ultraviolet absorbent -continued (UV-2)
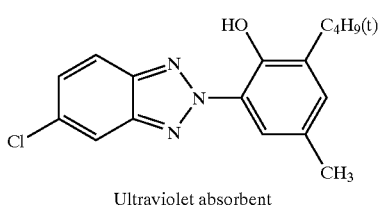
Ultraviolet absorbent (UV-3)
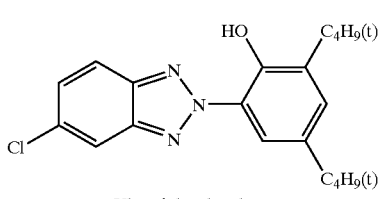
Ultraviolet absorbent (UV-4)
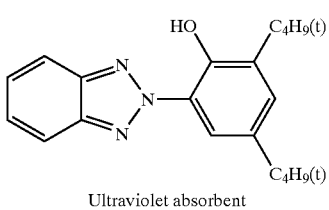
Ultraviolet absorbent (Solv-1)
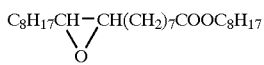

(Solv-2)
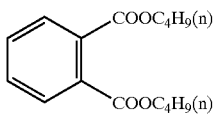

(Solv-3)
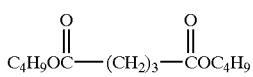

(Solv-4)
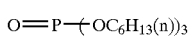

(Solv-5)
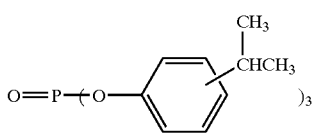

(Solv-6)
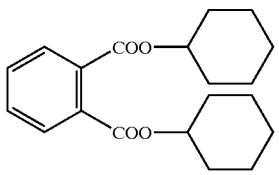

(Solv-7)
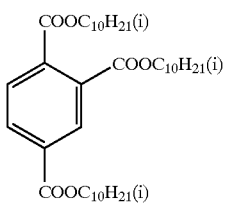

(3) Development Processing

The thus obtained lightsensitive material sample was formed into 127 mm wide rolls and, with the use of Minilab Printer Processor PP350 manufactured by Fuji Photo Film Co., Ltd., the lightsensitive material sample was subjected to imagewise exposure through an average-density negative film and continuous processing (running test) until the volume of color development replenisher used in the following processing steps became half (0.5-fold) the volume of color development tank.

| Processing Step | Temp. | Time | Qty. of replenisher |
|---|---|---|---|
| Color development | 38.5° C. | 45 sec | 45 mL |
| Bleach-fix | 38.0° C. | 45 sec | 35 mL |
| Rinse 1 | 38.0° C. | 20 sec | — |
| Rinse 2 | 38.0° C. | 20 sec | — |
| Rinse 3 | 38.0° C. | 20 sec | — |
| Rinse 4 | 38.0° C. | 20 sec | 121 mL |
| Drying | 80° C. | | |

(Note)
*The quantity of replenisher is per $m^2$ of lightsensitive material.
**For Rinse (3), there was installed Rinse Cleaning System RC50D manufactured by Fuji Photo Film Co., Ltd. Rinse solution was drawn from Rinse (3) and fed to reverse osmosis module (RC50D) by the use of a pump. Permeated water from the module was fed to Rinse (4), and the concentrate was returned to Rinse (3). Pump pressure was regulated so that the rate of solution fed to the reverse osmosis module was maintained at 50 to 300 mL/min. Circulation through the reverse osmosis module was effected at controlled temperature for 10 hr per day. Rinsing was performed by a 4-tank countercurrent system from Rinse (4) through Rinse (1).

The composition of each processing solution was as follows.

| (Color developer) | (Tank soln.) |
|---|---|
| Water | 800 mL |
| Compound of the invention | 2 mmol |
| Brightening agent (FL-1) | 0.35 g |
| Triisopropanolamine | 8.8 g |
| Polyethylene glycol (av. MW: 300) | 10.0 g |
| Ethylenediaminetetraacetic acid | 4.0 g |
| Sodium sulfite | 0.10 g |
| Potassium chloride | 10.0 g |
| Sodium 4,5-dihydroxybenzene-1,3-disulfonate | 0.50 g |
| Disodium-N,N-bis(sulfonatoethyl)hydroxylamine | 8.5 g |
| 4-Amino-3-methyl-N-ethyl-N-(β-methanesulfonamidoethyl)aniline.3/2sulfate.monohydrate | 4.8 g |
| Potassium carbonate | 26.3 g |
| Water | q.s. ad 1000 mL |
| pH (25° C., adjusted with sulfuric acid and KOH) | 10.15 |

A 3.8-fold aqueous dilution of color development composition prepared in item (1) above was used as the color development replenisher.

|  | (Tank soln.) | (Replenisher) |
|---|---|---|
| (Bleach-fix soln.) | | |
| Water | 800 mL | 800 mL |
| Ammonium thiosulfate (750 g/L) | 107 mL | 214 mL |
| m-Carboxybenzenesulfinic acid | 8.3 g | 16.5 g |
| Fe(III) ammonium ethylenediaminetetraacetate | 47.0 g | 94.0 g |
| Ethylenediaminetetraacetic acid | 1.4 g | 2.8 g |
| Nitric acid (67%) | 16.5 g | 33.0 g |

-continued

|  | (Tank soln.) | (Replenisher) |
|---|---|---|
| Imidazole | 14.6 g | 29.2 g |
| Ammonium sulfite | 16.0 g | 32.0 g |
| Potassium metabisulfite | 23.1 g | 46.2 g |
| Water | q.s. ad 1000 mL | |
| pH (25° C., adjusted with nitric acid and aqueous ammonia) | 6.5 | 6.5. |
| (Rinse soln.) | | |
| Sodium chloroisocyanurate | 0.02 g | 0.02 g |
| Deionized water (permittivity: 5 μs/cm or less) | 1000 mL | 1000 mL |
| pH (25° C.) | 6.5 | 6.5. |

(4) Estimation (i) Stability against deposit precipitation

Each prepared color development composition was placed in glass bottles, and stored at −5° C. and at room temperature for 4 weeks. A 5-grade estimation of test results was made by visually inspecting the condition of liquid after storage. Level of conspicuous deposit precipitation was judged as x x; level of clear deposit precipitation as x; level of slight deposition recognized as Δ; level of clouding but no deposit precipitation as o; and level of thorough transparency without any clouding and deposition recognized as @.

(ii) Photographic characteristics in color paper processing

With respect to an unexposed lightsensitive material sample after the development processing, a reflection spectrum thereof was produced with the use of spectrophotometer model U-3500 equipped with an integrating sphere of 150 mm diameter, manufactured by Hitachi, Ltd. Absorbance at 450 nm was measured on the reflection spectrum and designated $D_B$. Each sample was washed with the use of 40° C. distilled water for 5 min, dried and subjected to the same measurement.

The absorbance at 450 nm of the resultant sample was designated $D_{BW}$.

$\Delta D_B$ was calculated by the following formula, whereby the degree of stain attributed to residual sensitizing dyes was estimated.

$$\Delta D_B = D_B - D_{BW}.$$

(iii) Result

TABLE 1

| Sample | Added compound | Addition amount (mmol) | Estimation of precipitation (−5° C.) | Estimation of precipitation (Room temp.) | Estimation of photographic characteristics ($\Delta D_B$) | Remark |
|---|---|---|---|---|---|---|
| 1-1 | Non | — | ⊚ | ⊚ | 0.020 | Comp. |
| 1-2 | FL-2 | 15 | xx | x | 0.005 | Comp. |
| 1-3 | 3 | 15 | ⊚ | ⊚ | 0.007 | Inv. |
| 1-4 | 8 | 15 | o | ⊚ | 0.006 | Inv. |
| 1-5 | 15 | 15 | ⊚ | ⊚ | 0.009 | Inv. |

With respect to sample 1-2 (comparative example) produced with the use of compound FL-2, the degree of stain attributed to residual sensitizing dyes was similar to or on the level close to those of the samples produced with the use of compounds of the present invention, but deposit precipitation occurred upon storage of the processing composition. With respect to sample 1-1 (comparative example), no deposit precipitation occurred. Therefore, the deposit precipitation is attributable to the added compound.

The lightsensitive material having undergone the development processing wherein use was made of the processing composition of the present invention exhibited a low value with respect to the stain $\Delta D_B$ attributed to residual sensitizing dyes, namely, only a slight coloring of white ground. The processing composition of the present invention, even after storage for 4 weeks, was thoroughly transparent at room temperature, and was thoroughly transparent or in the state of slight clouding recognized at low temperature (−5° C.). Irrespective of the temperature, no deposit precipitation occurred. Therefore, it has become apparent that the present invention is excellent in the capability of reducing the stain attributed to sensitizing dyes remaining in the lightsensitive material after the processing, and that the processing composition of the present invention is a composition free of precipitation deposits during the low temperature storage of the processing composition.

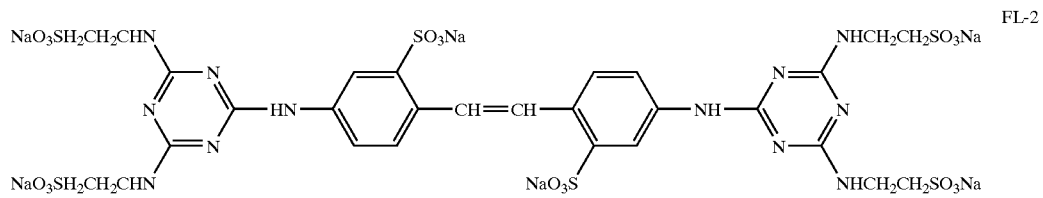

FL-2

EXAMPLE 2

(1) Preparation of bleach composition

| | |
|---|---|
| Water | 400 mL |
| Compound of the invention | Table 2 |
| m-Carboxybenzenesulfinic acid | 50.0 g |
| Fe(III) ammonium ethylenediaminetetraacetate | 210 g |
| Ethylenediaminetetraacetic acid | 7.5 g |
| Ammonium nitrate | 24.0 g |
| Water | q.s. ad 1000 mL |
| pH (25° C., adjusted with nitric acid and aqueous ammonia) | 6.00. |

(2) Preparation of fixing composition

| | |
|---|---|
| Compound of the invention | Table 3 |
| Ammonium thiosulfate (750 g/mL) | 575 mL |
| Imidazole | 7.5 g |
| Ethylenediaminetetraacetic acid | 9.0 g |
| Ammonium sulfite | 183 g |
| Water | q.s. ad 1000 mL |
| pH (25° C., adjusted with nitric acid and aqueous ammonia) | 6.00. |

(3) Development Processing

Development processing was carried out in the same manner as in Example 1. In the color development replenisher, use was made of a 3.8-fold aqueous dilution of the composition for sample 1-1 of Example 1. As the replenisher for bleach-fix solution, use was made of a 1.5-fold dilution of a 1:1 mixture of bleach composition prepared in item (1) above and fixing composition prepared in item (2) above. As the tank solution of bleach-fix solution, use was made of a 3-fold dilution of a 1:1 mixture of bleach composition prepared in item (1) above and fixing composition prepared in item (2) above. The combination of bleach composition and fixing composition was as indicated in Table 4.

(4) Estimation (i) Stability Against Deposit Precipitation

The same estimation as in Example 1 was effected.

(ii) Photographic Characteristics in Color Paper Processing

The same estimation as in Example 1 was effected.

(iii) Result

TABLE 2

| Sample | Added compound | Addition amount (mmol) | Estimation of precipitation (−5° C.) | Estimation of precipitation (Room temp.) | Remark |
|---|---|---|---|---|---|
| 2-1 | Non | — | ⊚ | ⊚ | Comp. |
| 2-2 | 3 | 6 | ○ | ○ | Inv. |
| 2-3 | 8 | 6 | ○ | ⊚ | Inv. |
| 2-4 | 12 | 6 | ○ | ⊚ | Inv. |
| 2-5 | 15 | 6 | ○ | ⊚ | Inv. |

TABLE 3

| Sample | Added compound | Addition amount (mmol) | Estimation of precipitation (−5° C.) | Estimation of precipitation (Room temp.) | Remark |
|---|---|---|---|---|---|
| 3-1 | Non | — | ⊚ | ⊚ | Comp. |
| 3-2 | 3 | 6 | ○ | ○ | Inv. |
| 3-3 | 8 | 6 | ○ | ⊚ | Inv. |
| 3-4 | 12 | 6 | ○ | ⊚ | Inv. |
| 3-5 | 15 | 6 | ○ | ⊚ | Inv. |

TABLE 4

| Bleach composition | Fixing composition | Estimation of photographic characteristics ($\Delta D_B$) | Remark |
|---|---|---|---|
| 2-1 | 3-1 | 0.020 | Comp. |
| 2-3 | 3-1 | 0.007 | Inv. |
| 2-3 | 3-3 | 0.005 | Inv. |
| 2-3 | 3-5 | 0.010 | Inv. |
| 2-5 | 3-5 | 0.007 | Inv. |

As apparent from Tables 2 and 3, each processing composition of the present invention, even after storage for 4 weeks, was thoroughly transparent at room temperature, and was thoroughly transparent or in the state of slight clouding recognized at low temperature (−5° C.). Irrespective of the temperature, no deposit precipitation occurred. As apparent from Table 4, the lightsensitive material having undergone the development processing wherein use was made of the processing composition of the present invention exhibited a low value with respect to the stain $\Delta D_B$ attributed to residual sensitizing dyes, namely, only a slight coloring of white ground. Therefore, it has become apparent that the present invention is excellent in the capability of reducing the stain attributed to sensitizing dyes remaining in the lightsensitive material after the processing, and that the processing composition of the present invention is a composition free of precipitation deposits during the low temperature storage of the processing composition.

As apparent from the foregoing detailed description, the processing composition for silver halide photographic lightsensitive material wherein the heterocycle combination of the general formula (I) is contained according to the present invention and the method of forming an image with the use of the processing composition enable exerting the advantageous effects of not only reducing stain attributed to sensitizing dyes remaining in the lightsensitive material after the processing thereof but also being free of any precipitation deposits during the low-temperature storage of the processing composition.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of forming an image, comprising using a photographic processing composition for silver halide color photographic lightsensitive material comprising at least one compound represented by formula (I):

$$A_1-X-L-Y-A_2. \qquad (I)$$

wherein each of $A_1$ and $A_2$ independently represents an aryl group or an aromatic heterocyclic group; L represents an aromatic heterocyclic group, with the proviso that a triazine ring is not represented thereby; and each of X and Y independently represents O, S or $NR_1$, wherein $R_1$ represents a hydrogen atom or an alkyl group having 1 to 6 carbon atoms, with the proviso that the molecule of the formula (I) has a substituent containing at least one of —OH, —$CO_2M$ and —$SO_3M$ groups, wherein M represents a hydrogen atom, an alkali metal, an alkaline earth metal, an ammonium or a pyridinium, and provided that the molecule of the formula (I) has no azo group.

2. A method of forming an image, comprising using the photographic processing composition for silver halide color photographic lightsensitive material according to claim 1, wherein, in the formula (I), L is a pyridinediyl group, a pyrazinediyl group, a pyrimidinediyl group, a pyridazinediyl group or a phthalazinediyl group.

3. A method of forming an image, comprising using the photographic processing composition for silver halide color photographic lightsensitive material according to claim 1, in color development processing.

4. A method of forming an image, comprising using the photographic processing composition for silver halide color photographic lightsensitive material according to claim 2, in color development processing.

5. A method of forming an image, comprising using the photographic processing composition for silver halide color photographic lightsensitive material according to claim 1, in bleach processing or bleach-fix processing.

6. A method of forming an image, comprising using the photographic processing composition for silver halide color photographic lightsensitive material according to claim 2, in bleach processing or bleach-fix processing.

7. A method of forming an image, comprising using the photographic processing composition for silver halide color photographic lightsensitive material according to claim 1, in fixing processing.

8. A method of forming an image, comprising using the photographic processing composition for silver halide color photographic lightsensitive material according to claim 2, in fixing processing.

9. A method of forming an image, comprising using the photographic processing composition for silver halide color photographic lightsensitive material according to claim 1, in a solution wherein the concentration of the compound represented by formula (I) is in a range of 0.05 to 20 mmol/L.

* * * * *